(12) United States Patent
Roth

(10) Patent No.: US 10,173,953 B2
(45) Date of Patent: Jan. 8, 2019

(54) METHOD AND DEVICE FOR PRODUCING L-MENTHOL IN SOLID FORM

(71) Applicant: SANDVIK MATERIALS TECHNOLOGY DEUTSCHLAND GMBH, Düsseldorf (DE)

(72) Inventor: Bernhard Roth, Affalterbach (DE)

(73) Assignee: SANDVIK MATERIALS TECHNOLOGY DEUTSCHLAND GMBH, Duesseldorf (DE)

( * ) Notice: Subject to any disclaimer, the term of this patent is extended or adjusted under 35 U.S.C. 154(b) by 0 days.

(21) Appl. No.: 15/508,411

(22) PCT Filed: Aug. 27, 2015

(86) PCT No.: PCT/EP2015/069610
§ 371 (c)(1),
(2) Date: Mar. 2, 2017

(87) PCT Pub. No.: WO2016/034481
PCT Pub. Date: Mar. 10, 2016

(65) Prior Publication Data
US 2017/0283349 A1    Oct. 5, 2017

(30) Foreign Application Priority Data
Sep. 3, 2014  (DE) .......... 10 2014 217 603

(51) Int. Cl.
*C07C 29/76*  (2006.01)
*C07C 35/12*  (2006.01)
(Continued)

(52) U.S. Cl.
CPC .......... *C07C 29/76* (2013.01); *B01J 2/20* (2013.01); *B01J 2/26* (2013.01); *C07B 2200/07* (2013.01); *C07C 2601/14* (2017.05)

(58) Field of Classification Search
CPC ...................................... C07C 29/76
See application file for complete search history.

(56) References Cited

U.S. PATENT DOCUMENTS 4,623,307 A  * 11/1986 Froeschke .......... B29B 9/10
249/102
8,288,593 B2  10/2012 Rauls et al.
(Continued)

FOREIGN PATENT DOCUMENTS

EP  0 145 839 A2  6/1985
EP  2 896 680 A1  7/2015
(Continued)

OTHER PUBLICATIONS

Korean Office Action issued in Appln. No. 10-2017-7008308 dated May 21, 2018 with English translation (18 pages).
(Continued)

*Primary Examiner* — Medhanit W Bahta
(74) *Attorney, Agent, or Firm* — Flynn Thiel, P.C.

(57) ABSTRACT

A process for producing L-menthol in solid form, including the following steps: providing a menthol melt, feeding the melt to a drop former having a rotating, perforated outer drum and a fixed nozzle strip adjacent to the inside of the outer drum, depositing the menthol melt produced by the drop former onto a continuous cooling belt, solidifying the menthol melt during transport on the cooling belt to form L-menthol pellets and taking the pellets off in the region of a deflection drum for the cooling belt.

11 Claims, 3 Drawing Sheets

Figure 1:
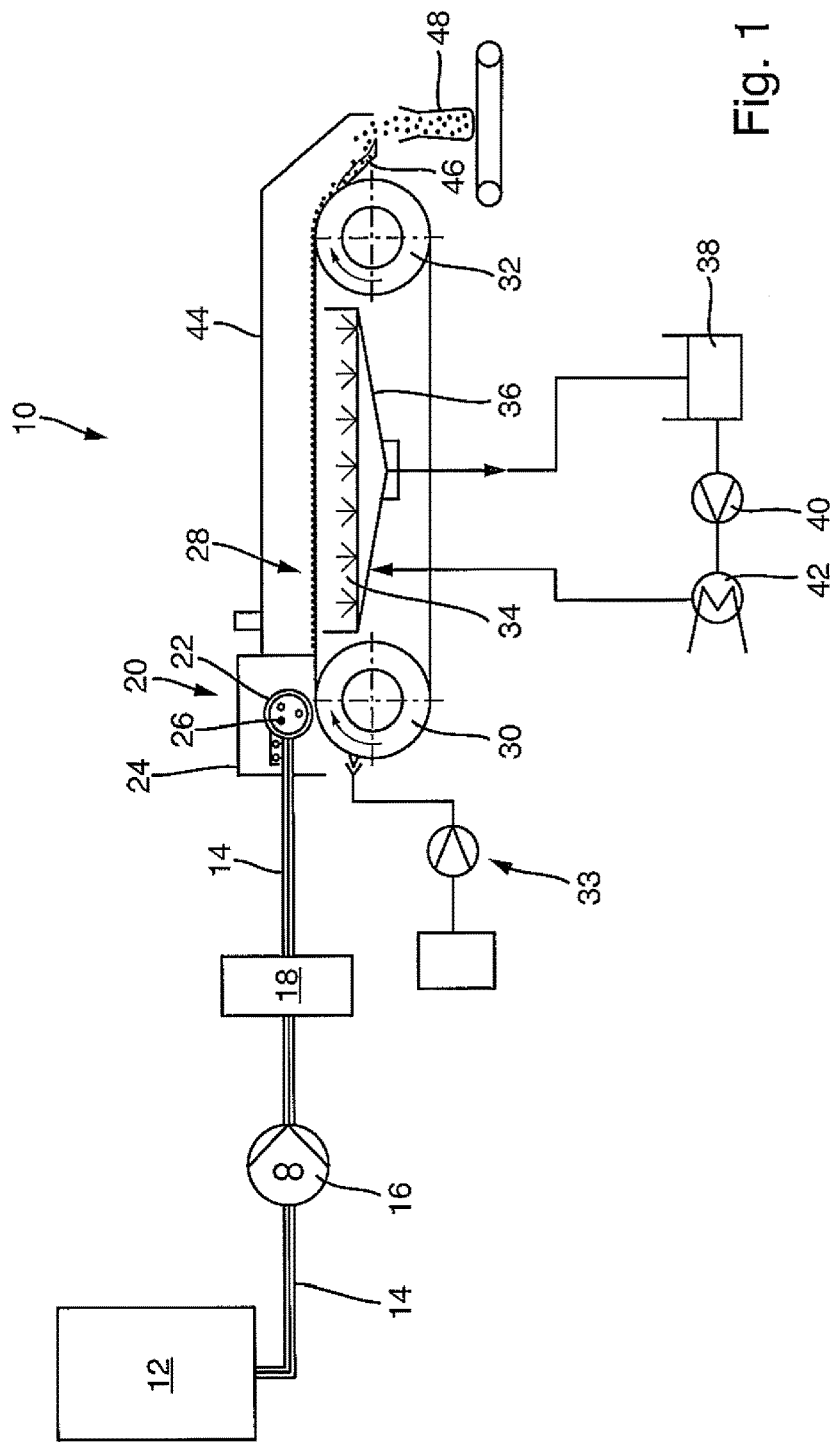

(51) Int. Cl.
*B01J 2/26* (2006.01)
*B01J 2/20* (2006.01)

(56) References Cited

U.S. PATENT DOCUMENTS

| | | |
|---|---|---|
| 8,785,698 B2 | 7/2014 | Nagaoka et al. |
| 9,366,485 B2 | 6/2016 | Schromm et al. |
| 2009/0011238 A1 | 1/2009 | Rheinlander et al. |
| 2009/0062427 A1 | 3/2009 | Tornow et al. |
| 2010/0185024 A1 | 7/2010 | Rauls et al. |
| 2011/0313205 A1 | 12/2011 | Nagaoka et al. |
| 2013/0112370 A1 | 5/2013 | Schromm et al. |
| 2014/0290290 A1 | 10/2014 | Nagaoka et al. |
| 2015/0166897 A1 | 6/2015 | Kleinhans et al. |

FOREIGN PATENT DOCUMENTS

| | | |
|---|---|---|
| KR | 10-2010-0080517 A | 7/2010 |
| WO | WO 2008/152009 A1 | 12/2008 |
| WO | WO 2010/095034 A1 | 8/2010 |
| WO | WO 2012/007331 A1 | 1/2012 |

OTHER PUBLICATIONS

Notification of Transmittal of International Search Report issued in Application No. PCT/EP2015/069610 dated Nov. 9, 2015 (1 page).
International Search Report issued in Application No. PCT/EP2015/069610 with English translation dated Nov. 9, 2015 (7 pages).
Written Opinion of International Searching Authority issued in Application No. PCT/EP2015/069610 dated Nov. 9, 2015 (5 pages).
Search Report of German Patent Office issued in Application No. 10 2014 217 603.4 dated Nov. 24, 2014 (7 pages).

\* cited by examiner

METHOD AND DEVICE FOR PRODUCING L-MENTHOL IN SOLID FORM

The invention relates to a process and an apparatus for producing L-menthol in solid form.

A process for producing L-menthol in solid form is already known from the international publication WO 2008/152009 A1. Menthol is a naturally occurring active compound which is widely employed in pharmacy, cosmetics and the food industry. In natural sources, for example peppermint oil, menthol occurs in the form of four diastereomeric pairs of enantiomers, of which only the main component, namely (-)-menthol or L-menthol, has the desired taste and other sensorial properties. It has long been known that L-menthol can crystallize in four different crystal modifications which have different physical properties for the same chemical composition. The melting points of these various modifications are in the range from 33° C. to 43° C. The melting point of the stable alpha modification is from 42° C. to 43° C. In general, all solids which, like L-menthol, have a melting point only barely above ambient temperature display a strong tendency to cake and form lumps. Contacting of an I-menthol melt with two cooled surfaces at a distance from one another is proposed. Such cooled surfaces can, for example, consist of continuous belts made of smooth or polished stainless steel. Double belt coolers are suitable for bringing the L-menthol melt simultaneously in contact with two cooled surfaces. Mixing the L-menthol melt with seed crystals is also proposed. Such seed crystals can be produced in a scratch cooler.

The invention aims to provide a process and an apparatus for producing L-menthol in solid form, with the L-menthol produced having improved storage properties.

The invention provides a process for producing L-menthol in solid form, in which the following steps are provided: providing a menthol melt, feeding the melt to a drop former having a rotating, perforated outer drum and a fixed nozzle strip adjacent to the inside of the outer drum, depositing melt drops produced by the drop former onto a continuous cooling belt, solidifying the melt drops during transport on the cooling belt to form L-menthol pellets and taking the pellets off in the region of a deflection drum for the cooling belt.

The invention is based on the recognition that smooth surfaces of the L-menthol ensure good storage properties which are stable over time. Furthermore, it was recognized by the inventors that pellets produced by solidifying melt drops have comparatively smooth surfaces on all sides and, in particular, have no broken edges, so that L-menthol pellets should in principle have good storage properties. The inventors have surprisingly been able to produce L-menthol pellets of satisfactory quality, i.e. pellets which have an approximately spherical shape and thus have a small surface area relative to the volume, by means of a drop former having a rotating, perforated outer drum and a fixed nozzle strip adjacent to the inside of the outer drum. The tendency for lumps to be formed during storage is also significantly reduced thereby. The inventors have been able to produce the drops of the menthol melt by means of the drop former with a sufficient viscosity for the drops not to spread out on deposition on the cooling belt. In addition, the inventors have been able to make do with simple deposition on a cooling belt having only one cooled surface for solidifying the drops of the menthol melt.

In an embodiment of the invention, the menthol melt is conveyed through a scraping cooler in order to produce seed crystals before the melt is fed to the drop former. It is advantageous for more than 10% by weight of seed crystals to be produced in the menthol melt in the scraping cooler. In particular, more than 20% by weight of seed crystals are produced in the menthol melt in the scraping cooler. An amount of seed crystals in the menthol melt which are produced in the scraping cooler is advantageously in the range from 30% by weight to 40% by weight. Such a proportion by weight of seed crystals in the menthol melt makes it possible to produce drops of the menthol melt in the drop former with a suitable viscosity so that these drops of melt do not spread out to form a flat pat on impingement on the cooling belt but instead retain an approximately spherical shape.

In an embodiment of the invention, a temperature in a range from 26° Celsius to 32° Celsius is set at the scraping surfaces of the scraping cooler.

Such a temperature range at the scraping surfaces of the scraping cooler represents, according to the experience of the inventors, the possible temperature range within which the scraping surfaces have to be kept in order firstly to produce the desired crystal configuration in a sufficient amount and secondly to prevent blockage of the scraping cooler by excessively large amounts of crystallized material.

In an embodiment of the invention, the menthol melt is conveyed in a circuit through the scraping cooler so that the menthol melt passes through the scraping cooler a plurality of times.

The residence times on the scraping surfaces of the scraping cooler necessary for producing large amounts of seed crystals can be achieved in this way. At the same time, the flow velocity of the menthol melt present in slurry form is kept high enough to prevent blockage of the scraping cooler due to excessive crystallization.

In an embodiment of the invention, an amount conveyed in the circuit through the scraping cooler is at least 10 times, in particular 20 times, an amount conveyed from the scraping cooler to the drop former.

In this way, the desired large amount of seed crystals can be produced and blockage of the scraping cooler is prevented.

In an embodiment of the invention, the scraping cooler is cooled by means of a liquid coolant, in particular water, with an amount of coolant conveyed through the scraping cooler being at least 10 times the amount of menthol melt conveyed through the scraping cooler.

The setting of the temperature at the scraping surfaces of the scraping cooler in the desired temperature range is ensured by a very large amount of coolant relative to the amount of menthol melt.

In an embodiment of the invention, the setting of a temperature of the liquid coolant is effected in a temperature control unit using hot cooling liquid or steam and cold cooling liquid.

In this way, fluctuations of the temperature of the cooling liquid can be evened out very quickly and it is possible both to heat and to cool in order to keep the temperature of the scraping surfaces in the desired narrow acceptable range.

In an embodiment of the invention, the menthol melt is conveyed through a precooler before the melt is fed to the drop former.

Setting of the desired viscosity of the menthol melt in the drop former is assisted in this way.

In an embodiment of the invention, the menthol melt is conveyed through a scraping cooler in order to produce seed crystals after conveying the menthol melt through the precooler and before feeding the melt to the drop former.

This assists the production of seed crystals in the scraping cooler since the menthol melt has been precooled before flowing into the scraping cooler.

In an embodiment of the invention, a temperature above the melting point of the menthol melt is set in the drop former so that crystallization of the menthol melt occurs in the drop former to only a very small extent and deposits are avoided.

Such setting of a predefined temperature in the drop former is essential to the success of the process of the invention. Here, the temperature has to be set within tight tolerances. For this purpose, channels for a medium for controlling the temperature of the nozzle strip are provided around the nozzle strip of the drop former, advantageously within a one-piece block or core of the drop former into which the nozzle strip is also integrated. On the one hand, the menthol melt has to be kept liquid or paste-like within the drop former so that no deposits are formed. On the other hand, the viscosity of the menthol melt has to be sufficiently high for the drops produced not to spread out immediately to form pats on impingement on the cooling belt. A temperature therefore has to be set very exactly to the desired temperature range within the drop former and especially in the region of a central feed channel and a nozzle strip of the drop former.

The problem addressed by the invention is also solved by an apparatus for producing L-menthol in solid form, which has means for providing a menthol melt, a drop former having a rotating, perforated outer drum and a fixed nozzle strip adjacent to the inside of the outer drum and also a continuous cooling belt arranged underneath the outer drum.

A scraping cooler for producing seed crystals in the menthol melt is advantageously arranged upstream of the drop former.

In an embodiment of the invention, the scraping cooler has a circular cylindrical, cooled interior surface which is scraped by scrapers arranged on a rotating shaft.

It has been found that scraping coolers configured in this way can produce sufficient amounts of seed crystals and nevertheless not tend to become blocked.

In an embodiment of the invention, a precooler for the menthol melt is arranged upstream of the scraping cooler.

Provision of a precooler assists the desired production of large amounts of seed crystals.

In an embodiment of the invention, the precooler, the scraping cooler and the drop former are provided with separate cooling liquid circuits.

This ensures maintenance of narrow acceptable temperature ranges in the precooler, in the scraping cooler and in the drop former.

In an embodiment of the invention, separate temperature control units are assigned to each of the cooling circuits, with each temperature control unit having a heating device for providing hot cooling liquid or steam and a cooling device for providing cold cooling liquid.

The temperature of the cooling liquid can be regulated very quickly and kept within a narrow temperature range by means of such temperature control units.

Figure 2:
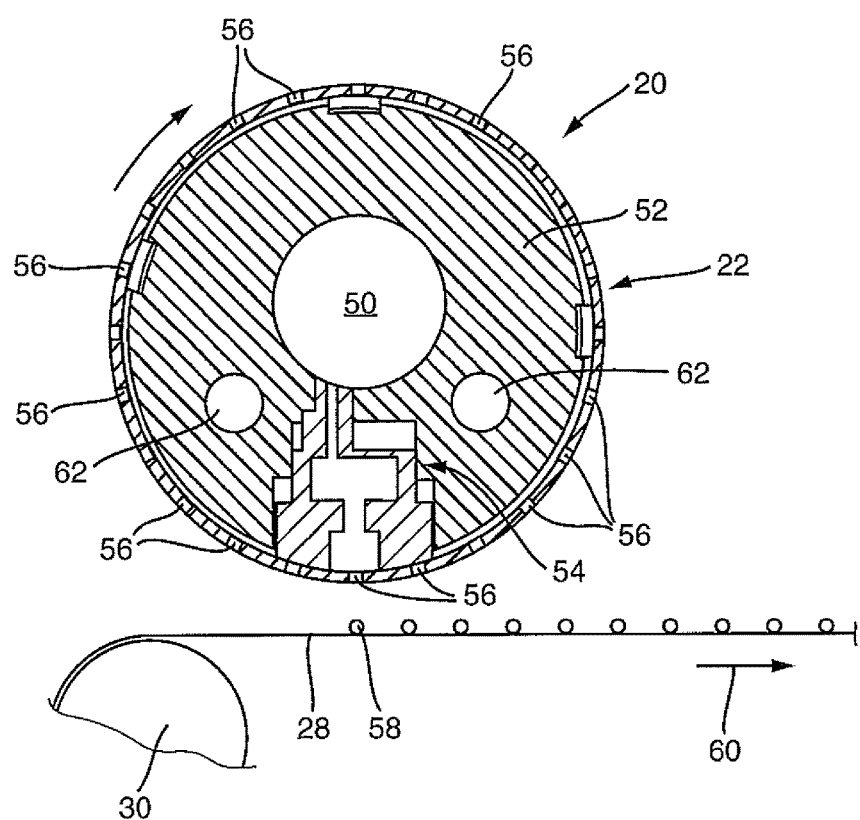

Further features and advantages of the invention can be derived from the claims and the following description of preferred embodiments of the invention in conjunction with the drawings. Individual features of the embodiments described and presented can be combined with one another in any way without going outside the scope of the invention. The drawings show:

FIG. 1 a schematic depiction of an apparatus according to the invention for producing L-menthol in solid form;

FIG. 2 an enlarged depiction of the drop former of the apparatus of FIG. 1; and

Figure 3:
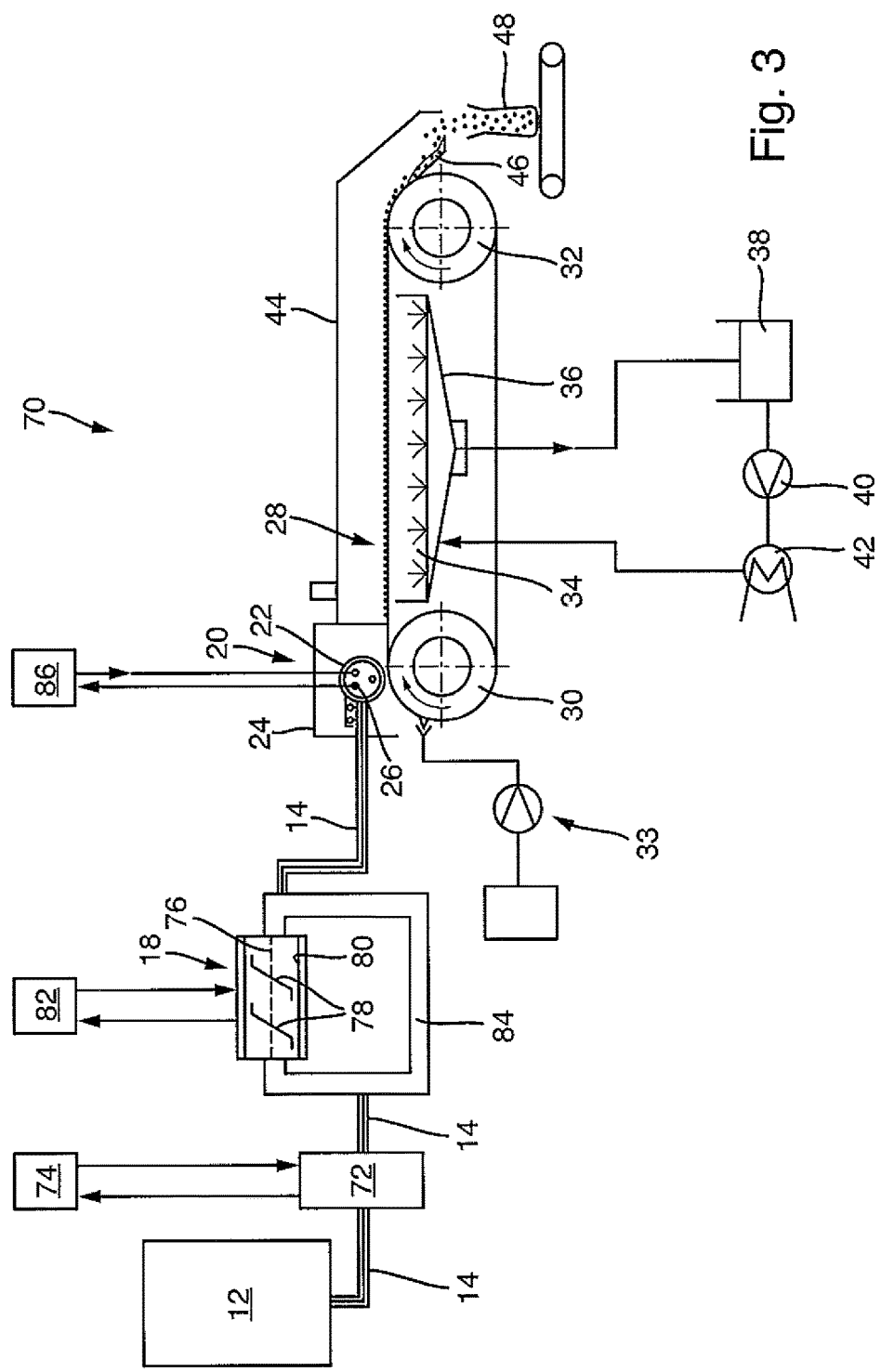

FIG. 3 a schematic depiction of an apparatus according to the invention for producing L-menthol in solid form, according to a further embodiment.

The schematic depiction in FIG. 1 shows an apparatus 10 for producing L-menthol in solid form. A menthol melt is produced by means of an apparatus 12 which is shown purely schematically. The menthol melt goes via a conduit 14 to a pump 16 and is then conveyed through a scraping cooler 18 in which seed crystals are produced in an amount of about 10% by weight of the menthol melt. The scraping cooler 18 has, in a known manner, at least one cooled surface at which the menthol melt partially crystallizes. According to the invention, the temperature of this cooled surface or scraping surface is kept in a small temperature range from 26° to 32°. These crystals are scraped off and thus added to the remaining menthol melt. The conduit 14, which can be heated or cooled, then leads further to a drop former 20 which has a rotating outer drum 22 and is arranged underneath a hood 24. A space underneath the hood 24 can be air-conditioned or maintained at a constant temperature. This is particularly advantageous in the pelletization of L-menthol since the outer surfaces of the rotating drum 22 of the drop former can thereby also be kept at a constant temperature.

The rotating outer drum 22 surrounds a fixed core of the drop former in which a nozzle strip which is not shown in FIG. 1 and also a plurality of channels 26 for passage of cooling liquid are provided. The drop former 20 is kept within a narrow acceptable temperature range by means of these channels or the cooling liquid conveyed therein. This temperature range is designed so that no deposits or only insignificant amounts of deposits of crystallized L-menthol melt are formed within the drop former 20 and, secondly, the L-menthol melt within the drop former 20 has a viscosity which is sufficiently high for the drops produced not to spread out immediately on impingement on a cooling belt arranged underneath the drop former 20, but instead retain a sphere-like shape.

The cooling belt 28 is configured as a continuous, circulating belt and is conveyed over two deflection drums 30, 32. The drop former 20 is arranged above the deflection drum 30 shown at left in FIG. 1. Menthol melt drops exiting from the rotating outer drum 22 of the drop former 20 are thus deposited on the upper span of the cooling belt 28 and then transported to the right in FIG. 1. Spray nozzles 32 are arranged underneath the upper span of the cooling belt 28 in order to spray a cooling liquid, in particular water, against the underside of the cooling belt 28. The cooling belt 28 advantageously consists of steel, in particular stainless steel, and thus ensures rapid cooling and solidification of the drops of the menthol melt deposited by the drop former 20 onto the cooling belt 28. The cooling water sprayed by the spray nozzles 32 against the underside of the cooling belt 28 is collected in a trough 36 and fed to a collection vessel 38. From the collection vessel 38, the cooling liquid is taken off by means of a pump 40, conveyed through a heat exchanger 42 which sets the desired temperature of the cooling liquid and from there is conveyed back to the spray nozzles 34.

The upper span of the cooling belt 28 on which the menthol melt drops are transported is surrounded in its region above the deflection drum 30 at left in FIG. 1 by the hood 24. Downstream of the hood 24, there is a further hood 44 which extends to over the region of the deflection drum 32 at right in FIG. 1. In this way, in addition to cooling of the cooling belt 28, a defined temperature can also be set above the cooling belt 28 so that the menthol melt drops deposited by the drop former 20 on the cooling belt 28 crystallize rapidly and in the desired configuration while the menthol melt drops on the cooling belt 28 move from the region of the left-hand deflection drum 30 to the region of the right-hand deflection drum 32.

At the right-hand deflection drum 32, the then solidified L-menthol pellets are taken off by means of an offtake knife 46 and, for example, packed in sacks 48.

A device 33 serves to apply a release agent upstream of the deposition point for the menthol melt drops in order to avoid strong adhesion of the drops to the cooling belt.

Owing to the sphere-like shape of the L-menthol pellets, these have a low surface area relative to the volume. In addition, the L-menthol pellets produced have a comparatively smooth surface which, in particular, has no broken edges. As a result of the small surface area and smooth surface, the storage properties of the L-menthol pellets produced are influenced extremely positively and the tendency of the pellets to cake is greatly reduced.

FIG. 2 shows a schematic sectional view of the drop former 20 of FIG. 1 with the cooling belt 28, which is only shown in part, arranged underneath the drop former 20. The menthol melt provided with seed crystals is fed to a central feed channel 50 in the core 52 of the drop former 20. The core 52 is configured as a solid circular cylinder whose external diameter is slightly smaller than the internal diameter of the perforated outer drum 22. The menthol melt fed in within the feed channel 50 is then conveyed further into a nozzle strip 54 which is adjacent to the inside of the perforated outer drum 22. By means of the nozzle strip 54, the menthol melt is pressed through openings 56 into the perforated outer drum 22. Each time one of the openings 56 runs past underneath the nozzle strip, a menthol melt drop 58 is thus produced and this is then, see FIG. 2, deposited underneath the nozzle strip 54 and the perforated outer drum 22 onto the upper side of the cooling belt 28. The upper span of the cooling belt 28 moves, as indicated by the arrow 60 in FIG. 2, from left to right and thus transports the menthol melt drops 58 out of the region underneath the drop former 20. In this way, rows of menthol melt drops 58 can be deposited successively on the cooling belt 28, as shown in FIG. 2.

The core 52 of the drop former 20 has, as shown in FIG. 2, two channels 62 for cooling liquid. These channels are arranged adjacent to the central feed channel 50 and the nozzle strip 54. The cooling liquid within these channels 62 keeps the core 52 within a narrow acceptable temperature range. As a result, the menthol melt provided with seed crystals can, both within the channel 50 and within the nozzle strip 54, be adjusted to a viscosity which ensures that the menthol melt drops 58 deposited on the cooling belt 28 have a sphere-like shape. At the same time, the temperature range of the core 52 is designed so that deposits within the channel 50 and the nozzle strip 54 are largely avoided.

The schematic depiction in FIG. 3 shows an apparatus according to the invention in a further embodiment. Constituents of the apparatus 70 which are identical to constituents of the apparatus 10 of FIG. 1 are not described again here.

In contrast to the apparatus 10 of FIG. 1, the conduit leads, downstream of the apparatus 12 for producing a menthol melt, firstly to a precooler 72. In this precooler 72, the menthol melt is cooled and brought into a temperature range which is advantageous for operation of the then downstream scraping cooler 18. The precooler 72 is provided with a temperature control unit 74 via which liquid coolant is conveyed to the precooler 72 and taken off from this again. The temperature in this coolant circuit between temperature control unit 74 and precooler 72 is set in the temperature control unit 74 by means of hot cooling liquid, in particular water, or vapor, in particular steam, and cold cooling liquid, in particular water. In this way, changeable cooling liquid temperatures in the return stream from the precooler 72 to the temperature control unit 74 can be reacted to very quickly and the temperature of the precooler 72 can be kept within a narrow acceptable temperature range.

The scraping cooler 18 is shown schematically in FIG. 3 and has a shaft 76 which is provided with scrapers 78 which scrape the circular cylindrical interior surface 80 of the scraping cooler 18. This circular cylindrical interior surface 80 is cooled to a temperature in the range from 26° Celsius to 32° Celsius in order to make crystallization of the menthol melt in the desired crystal configuration possible. The temperature of the interior surface 80 is set by means of a further temperature control unit 82 from which liquid coolant is circulated to the scraping cooler 18 and from the scraping cooler 18 to the temperature control unit 82. Setting of the temperature of the liquid coolant in the temperature control unit 82 is effected by means of hot cooling liquid, in particular water, or vapor, in particular steam, and cold cooling liquid, in particular water. This makes it possible to keep the temperature of the scraping surface 80 in the scraping cooler 18 within the temperature range from 26° Celsius to 32° Celsius.

The amount of the cooling liquid which is circulated by pumping and heated/cooled between the temperature control unit 82 and the scraping cooler 18 is at least 10 times the amount of menthol melt which is conveyed through the scraping cooler 18. A very small temperature range at the scraping cooler can be ensured in this way. The circuits between the temperature control unit 74 and the precooler 72 and between the temperature control unit 86 and the drop former 20 can also be configured in a corresponding manner.

Downstream of the precooler 72, the menthol melt is fed via the conduit 14 into a circulation conduit 84 which conveys the menthol melt to the scraping cooler 18 and from the scraping cooler 18 back to the inflow end of the scraping cooler 18. The further course of the conduit 14 then branches off from this circulation conduit 84 and then leads to the drop former 20. The amount of menthol melt which is conveyed in the circulation conduit 84 is at least 10 times the amount of menthol melt which is fed from the precooler 72 by the conduit 14 or is discharged via the conduit 14 in the direction of the drop former 20. In this way, the menthol melt passes a plurality of times through the scraping cooler 18 and the desired long residence times and as a result the production of a large amount of seed crystals, in particular in the range from 30% by weight to 40% by weight of the menthol melt, can be produced.

The pelletization of the menthol melt in the drop former 20 has been described above. To keep the drop former 20 at a desired temperature, a dedicated temperature control unit 86, which operates in the same way as the temperature control units 74, 82, is assigned to the drop former 20.

The invention claimed is:

1. A process for producing L-menthol in solid form, comprising the following steps:
    providing a menthol melt,
    feeding the melt to a drop former having a rotating, perforated outer drum and a fixed nozzle strip adjacent to the inside of the outer drum,
    depositing melt drops produced by the drop former onto a continuous cooling belt, solidifying the melt drops during transport on the cooling belt to form L-menthol pellets and taking the pellets off in the region of a deflection drum for the cooling belt.

2. The process as claimed in claim 1, including conveying the menthol melt through a scraping cooler before feeding the melt to the drop former in order to produce seed crystals.

3. The process as claimed in claim 2, including producing more than 10% by weight of seed crystals in the menthol melt in the scraping cooler.

4. The process as claimed in claim 3, including producing from 30 to 40% by weight of seed crystals in the menthol melt in the scraping cooler.

5. The process as claimed in claim 2, including setting a temperature at the scraping surfaces of the scraping cooler in a range from 26° Celsius to 32° Celsius.

6. The process as claimed in claim 2, including conveying the menthol melt in a circuit through the scraping cooler so that the menthol melt passes through the scraping cooler a plurality of times.

7. The process as claimed in claim 6, wherein an amount conveyed in the circuit through the scraping cooler is at least ten times an amount conveyed from the scraping cooler to the drop former.

8. The process as claimed in claim 2, wherein the scraping cooler is cooled by means of a liquid coolant with an amount of coolant conveyed through the scraping cooler being at least ten times the amount of menthol melt conveyed through the scraping cooler.

9. The process as claimed in claim 8, including setting a temperature of the liquid coolant in a temperature control unit using hot cooling liquid or steam and cold cooling liquid.

10. The process as claimed in claim 1, including conveying the menthol melt through a precooler before feeding the melt to the drop former.

11. The process as claimed in claim 10, including conveying the menthol melt through a scraping cooler in order to produce seed crystals after conveying the menthol melt through the precooler and before feeding the melt to the drop former.

* * * * *